United States Patent [19]
Michelotti et al.

[11] Patent Number: 5,981,435
[45] Date of Patent: Nov. 9, 1999

[54] METHODS FOR CONTROLLING ALGAE

[75] Inventors: Enrique Luis Michelotti, Fort Washington; David Hamilton Young, Ambler, both of Pa.

[73] Assignee: Rohm and Haas Company, Philadelphia, Pa.

[21] Appl. No.: 09/078,420

[22] Filed: May 14, 1998

Related U.S. Application Data

[60] Provisional application No. 60/048,010, May 29, 1997.

[51] Int. Cl.⁶ .......................... A01N 43/06; A01N 43/40; A01N 37/20
[52] U.S. Cl. .......................... 504/154; 504/155; 504/156; 504/159
[58] Field of Search ..................... 504/154, 155, 504/156, 159

[56] References Cited

U.S. PATENT DOCUMENTS

| | | | |
|---|---|---|---|
| 3,661,991 | 5/1972 | McNulty et al. | 260/588 D |
| 4,822,902 | 4/1989 | Carley et al. | 558/14 |
| 4,863,940 | 9/1989 | Sharma | 514/359 |
| 5,254,584 | 10/1993 | Michelotti et al. | 514/514 |
| 5,304,572 | 4/1994 | Michelotti et al. | 514/514 |
| 5,811,427 | 9/1998 | Michelotti et al. | 514/255 |
| 5,891,918 | 4/1999 | Michelotti et al. | 514/617 |

OTHER PUBLICATIONS

S. D. Strauss and P. R. Puckorius, Power, S1, "Cooling–Water Treatment for Control of Scaling, Fouling, Corrosion", Jun. 1984.

*Primary Examiner*—S. Mark Clardy
*Attorney, Agent, or Firm*—S. Matthew Cairns; Thomas D. Rogerson

[57] ABSTRACT

A method for controlling algae and marine fouling organisms is described. The method employs N-acetonylbenzamides compounds provided in an effective amount to kill or inhibit the growth of the algae or fouling organisms.

10 Claims, No Drawings

METHODS FOR CONTROLLING ALGAE

This is a nonprovisional application of prior pending provisional application Ser. No. 60/048,010 filed May 29, 1997.

The present invention relates to a method for controlling algae. In particular, the present invention relates to a method for controlling algae by the use of certain N-acetonylarylamide derivatives known to inhibit the growth of fungi, see, for example, U.S. Pat. Nos. 3,661,991; 4,822,902; 4,863,940; 5,254,584 and 5,304,572.

The presence of algae and other fouling organisms in various aqueous systems or systems exposed to water such as lattices, paints, coatings, cooling water systems, the marine environment, and decorative ponds can cause deterioration or disfigurement of the system. For example, painted surfaces may be disfigured by the unsightly buildup of algae, detracting from the overall aesthetics of the painted article and cooling towers or boats may lose efficiency due to the buildup of algae on surfaces. It is conventional to practice methods which inhibit the algal deterioration of such systems by incorporating a variety of additives or combinations of additives that are characterized by having antialgal activity.

A wide variety of materials have been used to control algae in different environments, including; chlorine/bromine compounds; glutaraldehyde, isothiazoles, organotin formulations; copper salts, quaternary ammonium compounds (see S. D. Strauss and P. R. Puckorius, *J. Power,* S1, June 1984); and triazines. However, each of these materials has deficiencies related to toxicity, pH and temperature sensitivity, limited effectiveness, chemical stability, and/or compatibility. Due to these deficiencies in conventional antialgal compounds, there is a continuing need for more effective antialgal agents.

We have discovered that N-acetonylarylamide derivatives inhibit the growth of algae. A first aspect of the present invention is a method for controlling algae, comprising applying to the locus of the algae an algicidally effective amount of one or more compounds of the structural formula I:

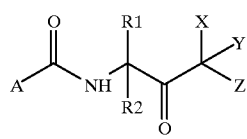

I wherein:

A is selected from substituted and unsubstituted phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, benzyl, $(C_3-C_7)$ cycloalkyl, $(C_1-C_6)$alkyl, halo$(C_1-C_6)$alkyl, $(C_2-C_6)$ alkenyl, halo$(C_2-C_6)$alkenyl, $(C_2-C_6)$alkynyl, and halo$(C_2-C_6)$alkynyl wherein the substituents are independently selected from:

a) one to four of halo, cyano, $(C_1-C_6)$alkyl, halo$(C_1-C_6)$ alkyl, $(C_2-C_6)$alkenyl, halo$(C_2-C_6)$alkenyl, $(C_2-C_6)$ alkynyl, halo$(C_2-C_6)$alkynyl, $(C_1-C_6)$alkoxy, halo $(C_1-C_6)$alkoxy, $(C_1-C_6)$alkylthio, halo$(C_1-C_6)$ alkylthio, nitro, $-NR^6R^7$, $-CR^8=NOR^9$, $NHCOOR^{10}$, $-CONR^{11}R^{12}$, $-COOR^{13}$;

b) fused 5, 6, and 7-membered rings formed from two such substituents; and c) fused 5, 6 and 7-membered carbocyclic rings which may contain up to two heteroatoms selected from the group consisting of: O, S, N, and P:

$R^1$ and $R^2$ are each independently selected from H, $(C_1-C_6)$alkyl, halo$(C_1-C_6)$alkyl, $(C_2-C_6)$alkenyl, halo $(C_2-C_6)$alkenyl, $(C_2-C_6)$alkynyl, or halo$(C_2-C_6)$alkynyl provided that at least one of $R^1$ and $R^2$ is other than H;

$R^6$ and $R^7$ are each independently selected from H, $(C_1-C_6)$alkyl, and $(C_1-C_6)$alkylcarbonyl;

$R^8$ is selected from H, $(C_1-C_6)$alkyl, $(C_2-C_6)$alkenyl, and $(C_2-C_6)$alkynyl;

$R^9$ is selected from H, $(C_1-C_6)$alkyl, $(C_2-C_6)$alkenyl, $(C_2-C_6)$alkynyl, and $(C_1-C_4)$alkylcarbonyl;

$R^{10}$, $R^{11}$, $R^{12}$ and $R^{13}$ are each independently selected from H, $(C_1-C_6)$alkyl, $(C_2-C_6)$alkenyl, and $(C_2-C_6)$alkynyl; and X, Y and Z are each independently selected from H, halo, cyano, thiocyano, isothiocyano and $(C_1-C_6)$ alkylsulfonyloxy, provided that at least one of X, Y and Z is halo, cyano, thiocyano, isothiocyano or $(C_1-C_6)$ alkylsulfonyloxy;

enantiomers and stereoisomers thereof; and acid addition salts thereof.

As used herein, the term "halo" means fluoro, bromo, chloro, or iodo.

The term "$(C_1-C_6)$alkyl" means a straight or branched saturated hydrocarbon group having from 1 to 6 carbons per group, and includes, e.g, methyl, ethyl, n-propyl, isopropyl, n-butyl, isobutyl, t-butyl, n-pentyl and n-hexyl. Halosubstituted alkyl groups, referred to as haloalkyl, include, for example, chloromethyl, trifluoromethyl, bromoethyl, pentafluoroethyl, iodopropyl, and chlorobutyl.

The term "$(C_2-C_6)$alkenyl" means a straight or branched group having at least one double bond and from 2 to 6 carbons per group, and includes, e.g, ethenyl, 2-propenyl, 2-butenyl and 2-methyl-2-propenyl.

The term "$(C_2-C_6)$alkynyl" means a straight or branched alkynyl group having at least one triple bond and from 2 to 6 carbons per group, and includes, e.g, ethynyl, 2-propynyl and 2-butynyl.

The term "$(C_1-C_6)$alkoxy" means a straight or branched alkoxy having from 1 to 6 carbons per group, and includes, e.g, methoxy, n-propoxy, iso-propoxy, n-butoxy, and t-butoxy.

The term "$(C_1-C_6)$alkylthio" means a straight or branched alkylthio group having from 1 to 6 carbons per group, and includes, e.g., methylthio and propylthio.

"Haloalkyl", "haloalkenyl", "haloalkynyl", "haloalkoxy", and "haloalkylthio" groups are "alkyl," "alkenyl," "alkynyl," "alkoxy" and "alkylthio" groups, respectively, which have from 1 to 5 halogen substituents.

The term "$(C_3-C_7)$ cycloalkyl" includes, for example, cyclopropyl and cyclohexyl.

The term "$(C_1-C_6)$alkylcarbonyl" includes straight or branched alkyl groups having from 1 to 6 carbons per group which are connected to a carbonyl group, for example, methylcarbonyl and butylcarbonyl.

The term "$(C_1-C_6)$alkylsulfonyloxy" includes straight or branched alkyl groups having from 1 to 6 carbon atoms per group which are connected to a sulfonyloxy group, for example, methylsulfonyloxy and propylsulfonyloxy.

Suitable $-NR_6R_7$ moieties include amino, monosubstituted amino and disubstituted amino such as, for example, amino, methylamino, ethylamino, acetylamino, and diethylamino.

The term "nitro" means a group having the structural formula $-NO_2$.

The term "cyano" means a group having the structural formula $-CN$.

The term "thiocyano" means a group having the structural formula —SCN.

The term "isothiocyano" means a group having the structural formula —NCS.

Suitable —$CR_8$=$NOR_9$ moieties include, for example, hydroximinomethyl, methoxyiminomethyl, ethoxyiminomethyl, methoxyiminoethyl, and methylcarbonyloxyiminomethyl.

Suitable —$CONR^{11}R^{12}$ substituents include amido (—$CONH_2$), monosubstituted amido and disubstituted amido such as, for example, methylamido (—$CONHCH_3$), dimethylamido (—$CON(CH_3)_2$), propylamido, and dibutylamido.

Suitable $NHCOOR^{10}$ substituents include, for example, methylcarbamate and isopropylcarbamate.

Also contemplated for use in the method of the present invention are compounds having the structural formula (II) wherein $R^4$ and $R^5$ together form a fused 5, 6, or 7-membered ring, which may contain up to two heteroatoms selected from the group consisting of O, S, N, and P; $R^1$ and $R^2$ are H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H; $R^3$ is selected from H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxy, $(C_1-C_6)$alkylthio, halo$(C_1-C_6)$alkoxy, nitro, carboxyl, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or $(C_1-C_6)$ alkyl, and X and Y are each independently selected from H, halo, cyano, thiocyano, isothiocyano and $(C_1-C_6)$ alkysulfonyloxy, provided that at least one of X and Y is not H.

The term "locus of the algae" means the algae itself and the environment where the algae grow or may grow (the system). Such environments include, for example, surfaces, bodies of water, plant foliage, and man-made structures.

Preferably, A is selected from substituted and unsubstituted phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, benzyl, and $(C_3-C_7)$cycloalkyl.

In a preferred embodiment of the method of the present invention, the compounds have the structural formula II,:

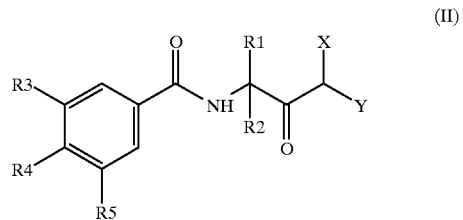

(II)

wherein:

$R^1$ and $R^2$ are each independently selected from H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is other than H;

$R^3$, $R^4$, and $R^5$ are each independently selected from H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxy, $(C_1-C_6)$alkylthio, halo$(C_1-C_6)$alkoxy, nitro, —$NR^6R^7$, —$CR^8$=$NOR^9$, $NHCOOR^{10}$, —$CONR^{11}R^{12}$, and —$COOR^{13}$;

$R^6$, $R^7$, $R^8$, $R^9$, $R^{10}$, $R^{11}$, $R^{12}$, and $R^{13}$ are each independently selected from H and $(C_1-C_6)$ alkyl; and X and Y are each independently selected from H, halo, cyano, thiocyano, isithiocyano and $(C_1-C_6)$ alkysulfonyloxy, provided that at least one of X and Y is other than H.

In a particularly preferred embodiment of the method of the present invention, the compounds used have the structural formula (II), wherein X is chloro or thiocyano; Y is H; $R^1$ is methyl; $R^2$ is selected from methyl and ethyl; $R^3$ and $R^5$ are each independently selected from H, halo, methyl, nitro, cyano, amino, —CH=$NOCH_3$ and —$NHCOOCH_3$, and $R^4$ is selected from H, halo, amino, cyano, —CH=$NOCH_3$, —$NHCOOCH_3$, $COOCH_3$, and $(C_1-C_4)$ alkyl.

In an even more preferred embodiment of the method of the present invention, the compounds have the structural formula (II), wherein X is chloro or thiocyano, Y is H, $R^1$ is methyl, $R^2$ is methyl or ethyl, $R^3$ and $R^5$ are each independently selected from halo, methyl, cyano and —CH=$NOCH_3$, and $R^4$ is H, halo, amino, methyl, or —CH=$NOCH_3$.

In an alternative embodiment, the method of the present invention uses compounds having the structural formula III:

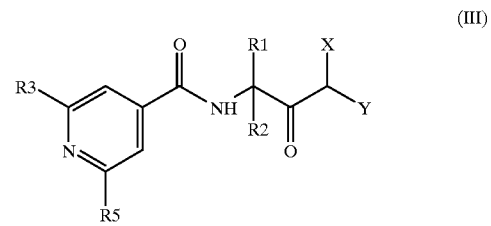

(III)

wherein $R^1$ and $R^2$ are H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H;

$R^3$ and $R^5$ are each independently selected from H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxy, $(C_1-C_6)$alkylthio, halo$(C_1-C_6)$alkoxy, nitro, carboxyl, —$NR^6R^7$, —$CR^8$=$NOR^9$, $NHCOOR^{10}$, —$CONR^{11}R^{12}$, and —$COOR^{13}$;

$R^6$, $R^7$, $R^8$, $R^9$, $R^{10}$, $R^{11}$, $R^{12}$, and $R^{13}$ are H or $(C_1-C_6)$ alkyl; and X and Y are each independently selected from H, halo, cyano, thiocyano, isothiocyano and $(C_1-C_6)$ alkysulfonyloxy, provided that at least one of X and Y is not H.

In another embodiment of the method of the present invention, the compounds have the structural formula IV:

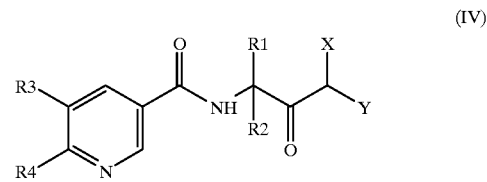

(IV)

wherein:

$R^1$ and $R^2$ are independently selected from H, $(C_1-C_6)$ alkyl, halo$(C_1-C_6)$alkyl, $(C_2-C_6)$alkenyl, and $(C_2-C_6)$ alkynyl, provided that at least one of $R^1$ and $R^2$ is other than H;

$R^3$ and $R^4$, are each independently selected from:

a) H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxy, $(C_1-C_6)$alkylthio, halo$(C_1-C_6)$alkoxy, nitro, —$NR^6R^7$, —$CR^8$=$NOR^9$, $NHCOOR^{10}$, —$CONR^{11}R^{12}$, and —$COOR^{13}$; and b) together form a fused 5, 6 or 7-membered carbocyclic ring which may contain up to two heteroatoms selected from the group consisting of: O, S, N, and P;

$R^6$, $R^7$, $R^8$, $R^9$, $R^{10}$, $R^{11}$, $R^{12}$, and $R^{13}$ are H or $(C_1-C_6)$ alkyl; and X and Y are each independently selected from H, halo, cyano, thiocyano, isothiocyano and $(C_1-C_6)$ alkysulfonyloxy, provided that at least one of X and Y is other than H.

In another embodiment of the method of the present invention, the compounds have the structural formula V:

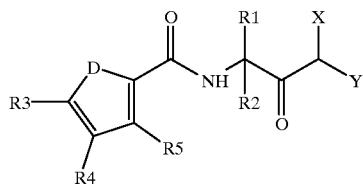

(V)

wherein:

D is O or S;

$R^1$ and $R^2$ are each independently selected from H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is other than H;

$R^3$, $R^4$, and $R^5$ are each independently selected from:

a) H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxy, $(C_1-C_6)$alkylthio, halo$(C_1-C_6)$alkoxy, nitro, —$NR^6R^7$, —$CR^8=NOR^9$, $NHCOOR^{10}$, —$CONR^{11}R^{12,}$ and —$COOR^{13}$; and b) two together form a fused 5, 6 or 7-membered carbocyclic ring which may contain up to two heteroatoms selected from the group consisting of: O, S, N, and P;

$R^6$, $R^7$, $R^8$, $R^9$, $R^{10}$, $R^{11}$, $R^{12}$, and $R^{13}$ are each independently selected from H and $(C_1-C_6)$ alkyl; and X and Y are each independently selected from H, halo, cyano, thiocyano, isithiocyano and $(C_1-C_6)$ alkysulfonyloxy, provided that at least one of X and Y is other than H.

In another embodiment, the method of the present invention uses compounds having the structural formula VI:

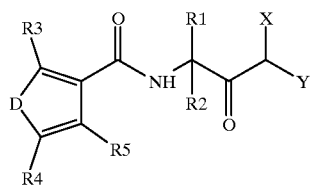

(VI)

wherein:

D is O or S;

$R^1$ and $R^2$ are each independently selected from H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is other than H;

$R^3$, $R^4$, and $R^5$ are each independently selected from:

a) H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxy, $(C_1-C_6)$alkylthio, halo$(Cl-C_6)$alkoxy, nitro, —$NR_6R_7$, —$CR^8=NOR^9$, $NHCOOR^{10}$, —$CONR^{11}R^{12}$, and —$COOR^{13}$; and b) $R^4$ and $R^5$ together form a fused 5, 6 or 7-membered carbocyclic ring which may contain up to two heteroatoms selected from the group consisting of: O, S, N, and P:

$R^6$, $R^7$, $R^8$, $R^9$, $R^{10}$, $R^{11}$, $R^{12}$, and $R^{13}$ are each independently selected from H and $(C_1-C_6)$ alkyl; and X and Y are each independently selected from H, halo, cyano, thiocyano, isithiocyano and $(C_1-C_6)$ alkysulfonyloxy, provided that at least one of X and Y is other than H.

When $R^1$ and $R^2$ are different, optical enantiomers of the compounds of the present invention are possible due to the presence of an asymmetric carbon atom linking $R^1$ and $R^2$. It is known that many biologically active compounds have optical enantiomers, one of which is more active than the other. Similarly, for compounds used in the method of the present invention, the biological activity of one enantiomer may exceed that of the other enantiomer. In such cases, both enantiomers are within the scope of the present invention. The enantiomers are known as "S" enantiomers and "R" enantiomers. The term "S enantiomer" means that the four groups on the carbon to which $R^1$ and $R^2$ are attached, when ranked according to the set of sequence rules of the Cahn-Ingold-Prelog system (*Angew. Chem. Int. Ed. Engl.* 5, 385–415 (1966)), define the carbon as having an S configuration. The term "R enantiomer" means that the four groups form an R configuration.

Algae which may be controlled by the method of the present invention include individual species and mixed cultures. Examples of species controlled include green algae such as *Chlorella pyrenoidosa, Scenedesmus quadricauda, Chlorococcum oleofaciens,* and Selenastrum species; blue-green algae (cyanobacteria) such as Phormidium species, *Anabaena flos-aquae, Nostoc commune,* Osilliatorae species, and Synechococcus species; and marine algae such as *Dunaliella parva*.

According to the method of the present invention, the effective compounds described herein may be combined with other known antialgal compounds including; chlorine/bromine compounds; glutaraldehyde, isothiazoles, isothiazolones, organotin formulations, copper salts, quaternary ammonium compounds; and triazines. When used in such combinations, the ratio of the compound or compounds to the other known antialgal compounds may vary from 99:1 to 1:99.

The amount of active ingredient required to control algae will depend upon many factors such as, for example; the type of surface; the amount of water present; whether the compound is incorporated into a coating composition, applied directly to an object, or added to an aqueous or other solution; and the type and extent of algal infestation. In general, an effective concentration of active ingredient will be from 5 to 50,000 parts per million (ppm). Unless otherwise stated, all weights given herein refer to the compounds themselves and not the weight of any formulation of the compounds.

While the compounds described herein may be administered alone to control algae, it is preferable to administer them as formulations. Useful formulations comprise one or more compounds and one or more acceptable carriers. The term "acceptable carrier" means a carrier compatible with the compound and other ingredients of the formulation and which is not toxic to the system or which will not cause degradation of the system. Formulations of the compounds may contain from 0.01 to 99.9 percent by weight of the compound. More typically the solutions and formulations will contain from 1.0 to 85 percent by weight of the compound. Useful formulations include aqueous solutions, solvent based solutions, wettable powders, emulsifiable concentrates, dusts, granular formulations, pellets, aerosols, or flowable emulsion concentrates. In such formulations, the compounds are extended with liquid or solid carriers and, when desired, suitable surfactants are incorporated.

In the case of spray formulations, it is often desirable to include one or more adjuvants, such as wetting agents, spreading agents, dispersing agents, stickers, adhesives, emulsifying agents and the like. Such adjuvants commonly used in the art can be found in the John W. McCutcheon, Inc. publication *Detergents and Emulsifiers, Annual,* Allured Publishing Company, Ridgewood, N.J., U.S.A. Spray formulations can be administered using common application methods, such as conventional high-volume hydraulic sprays, low-volume sprays, air-blast spray, aerial sprays, backpack and hand held sprays, and dusts. The dilution and rate of application will depend upon the type of equipment employed, the method of application, area treated, and algae to be controlled.

The compounds of the present invention may also be used to control algae in cooling tower water. In such applications the compound is maintained at a concentration of from 0.1 ppm to the solubility limit of the compound, preferably 1.0 to 200 ppm.

In addition, the compounds of the present invention are useful for imparting algal resistance to coatings or impregnant compositions. In such applications, the compound is incorporated into the coating or into the impregnating composition at a concentration from 0.1 to 10 percent by weight, preferably 1 to 5 percent by weight.

The compounds of the present invention may also useful for imparting algal resistance to construction products such as stucco, roof mastics, wall mastics, and masonry coatings; in clear finishes and coatings to protect underlying substrates from algae; for algae control in aquaculture including aquaria, fish hatcheries, shrimp ponds, finfish ponds, mollusk and crustacean cultivation; for algae control in recreational and decorative bodies of water such as swimming pools, lakes, fountains, and decorative ponds; for algae control in bodies of water for industrial or municipal use, such as settling or separation ponds, waste treatment ponds, and water reservoirs; for algae control in hydroponic farming; for algae control in processing and manufacture of pulp and paper products; and for inclusion in plastics or in coatings for plastics to protect against algae. Care must be taken in the selection of compound and application rate to avoid adverse effects on non-target organisms.

In addition to controlling algae, compounds of this invention have shown the ability to control organisms associated with the larval stages of organisms that cause hard fouling on submerged surfaces. For this reason, compounds of the invention are also useful as marine antifoulants.

Particular compounds useful in the method of the present invention include those compounds listed in Tables 1–3.

In Table 1 are shown compounds having the structural formula II).

TABLE 1

| Compound | R1 | R2 | R3 | R4 | R5 | x | y |
|---|---|---|---|---|---|---|---|
| 1 | CH$_3$ | C$_2$H$_5$ | Br | H | H | Br | Br |
| 2 | CH$_3$ | C$_2$H$_5$ | CH = NOCH$_3$ | NH$_2$ | Cl | Cl | H |
| 3 | CH$_3$ | C$_2$H$_5$ | CH = NOCH$_3$ | H | H | Cl | H |
| 4 | CH$_3$ | C$_2$H$_5$ | Cl | H | CH$_3$ | Cl | H |
| 5 | CH$_3$ | C$_2$H$_5$ | Cl | F | Cl | Cl | H |
| 6 | CH$_3$ | C$_2$H$_5$ | Cl | H | Br | Br | Br |
| 7 | CH$_3$ | CH$_3$ | Cl | H | Cl | SCN | H |
| 8 | CH$_3$ | CH$_3$ | Cl | H | Cl | Cl | H |
| 9 | CH$_3$ | C$_2$H$_5$ | Cl | CH$_3$ | Cl | Cl | H |
| 10 | CH$_3$ | CH$_3$ | Br | H | H | Br | Br |

TABLE 1-continued

| Compound | R1 | R2 | R3 | R4 | R5 | x | y |
|---|---|---|---|---|---|---|---|
| 11 | CH$_3$ | CH$_3$ | Br | H | H | Br | Cl |
| 12 | CH$_3$ | C$_2$H$_5$ | Br | H | H | Br | Cl |
| 13 | CH$_3$ | C$_2$H$_5$ | Cl | H | Cl | Cl | H |
| 14 | CH$_3$ | CH$_3$ | Cl | H | Cl | Br | Br |
| 15 | CH$_3$ | CH$_3$ | Cl | H | Cl | Br | H |
| 16 | CH$_3$ | CH$_3$ | Cl | H | Cl | NCS | H |
| 17 | CH$_3$ | C$_2$H$_5$ | Br | H | CH$_3$ | Cl | H |

In Table 2 is shown a compound having the structural formula (II), wherein $R^4$ and $R^5$ together form a fused ring.

TABLE 2

| Compound | R1 | R2 | R3 | R4R5 | x | y |
|---|---|---|---|---|---|---|
| 18 | CH$_3$ | C$_2$H$_5$ | Cl | —N = CH—O— | Cl | H |

Methods Used in Preparing Compounds

Compounds 1, 4, 5, 6, 7, 8, 10, 11, 12, 13, 14, 15, 16, and 17

Compounds 1, 4, 5, 6, 7, 8, 10, 11, 12, 13, 14, 15, 16, and 17 were prepared according to synthetic methods described in U.S. Pat. No. 4,822,902.

Compound 2

Compound 2 was prepared by reaction of the benzoyl chloride VII, in which R3 is Cl, R4 is NH$_2$ and R5 is CHNOCH$_3$, with the α-amino-α'-chloroketone derivative VIII, in which R1 is methyl and R2 is ethyl, as illustrated in Scheme A:

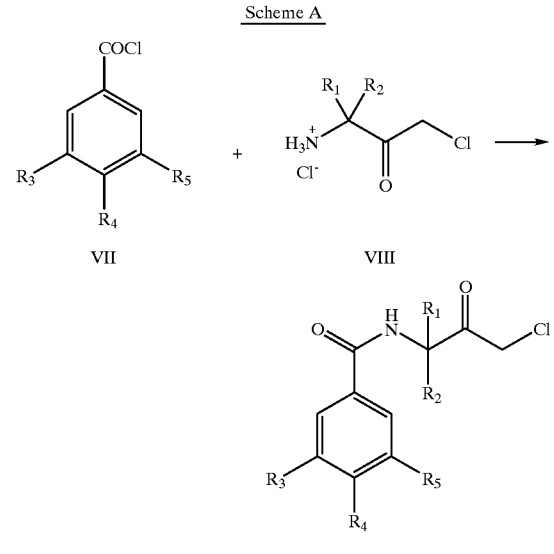

The starting benzoyl chloride used to prepare compound 2 can be prepared as indicated below in scheme B.

Scheme B

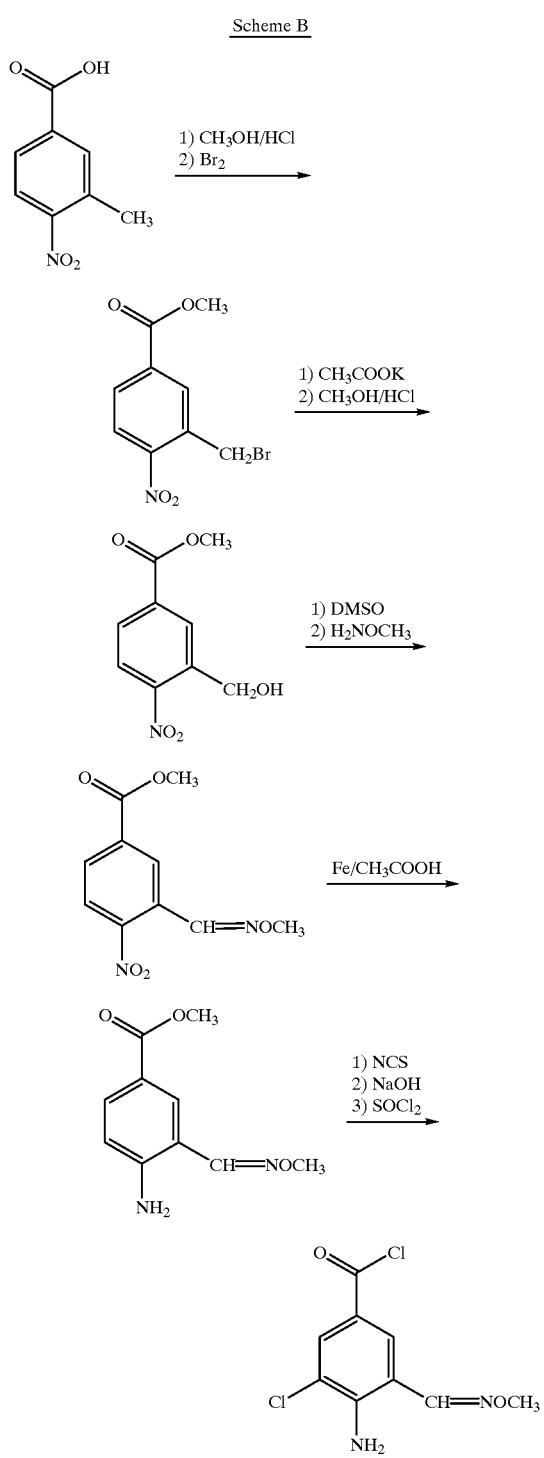

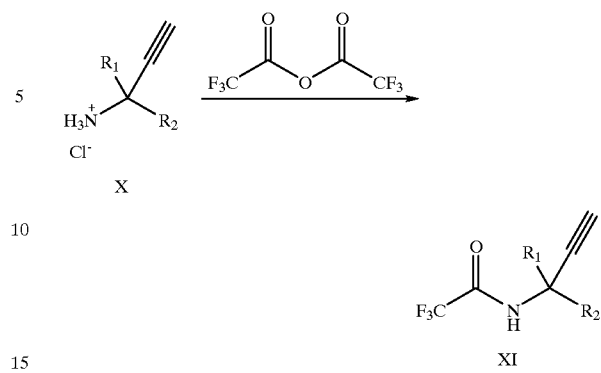

Treatment of the acetylenic amide XI with chlorine or a chlorine source at a temperature of from −78° C. to 0° C. in the presence of a solvent such as methylene chloride or chloroform yields the intermediate oxazoline (XIII). The oxazoline XII may be readily hydrolyzed under acidic conditions using an acid such as hydrochloric acid or sulfuric acid with a solvent such as methanol or tetrahydrofuran at a temperature of from 40° C. to 60° C., yielding the α-amino-α', α'-dichloroketone (XIII).

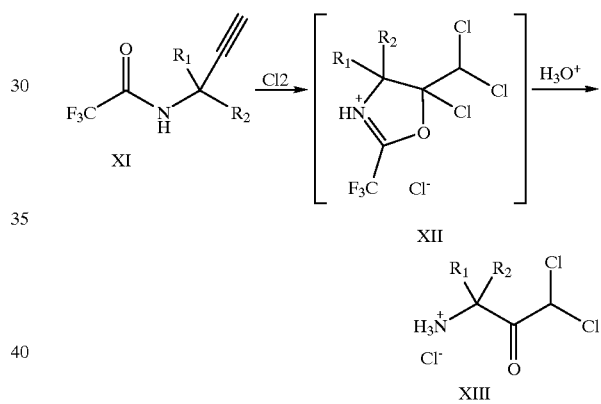

Selective catalytic dehalogenation of XIII yields the respective α-amino-α'-chloroketone derivative VIII:

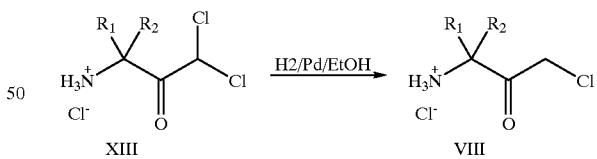

Experimental Procedures

Preparation of 4-amino-3-chloro-5-methoxyiminomethyl-N-(3-chloro-1-ethyl-1-methyl-2-oxoprovyl)benzamide (compound 2)

a) Preparation of methyl 3-methyl-4-nitrobenzoate.

In a 5-liter three-necked round-bottomed flask equipped with a reflux condenser, overhead stirrer and gas inlet, was placed 300 g of 3-methyl-4-nitrobenzoic acid and 3 l of methanol. To the resulting well-stirred solution was bubbled in 20.8 g of hydrogen chloride and the resulting mixture was refluxed for 3 hours. The reaction mixture was cooled to room temperature and allowed to stand overnight. The Compound VIII can be prepared by treating the acetylenic amine (X) with trifluoracetic anhydride in the presence of a solvent such as methylene chloride, chloroform, ethyl ether, or water and a base such as triethylamine, sodium carbonate, sodium bicarbonate, or sodium hydroxide to yield the acetylenic amide XI:

expected methyl 3-methyl-4-nitrobenzoate precipitated as light yellow crystals, which were collected by suction filtration yielding after drying 259.3 g. This solid was used as such in the next step.

b) Preparation of methyl 3-bromomethyl-4-nitrobenzoate.

In a 5-liter three-necked round-bottomed flask equipped with a reflux condenser, overhead stirrer, addition funnel and nitrogen inlet, was placed 220 g of methyl 3-methyl-4-nitrobenzoate, 2 l of anhydrous carbon tetrachloride and 4 g of benzoyl peroxide. To the resulting solution, irradiated with a 275 watt UV light, was added 198 g of bromine dropwise over a period of 2 hours at reflux. After the addition was complete the reaction mixture was refluxed for an additional 60 hours. The reaction mixture was cooled to room temperature. The solid which formed was separated by suction filtration. This solid (159.1 g) consisted of the expected methyl 3-bromomethyl-4-nitrobenzoate with minor amounts of the starting material. The mother liquors together with another 220 g of methyl 3-methyl-4-nitrobenzoate and 4 g of benzoyl peroxide were returned to the flask and treated with 198 g of bromine as described above. After the addition was complete the reaction mixture was refluxed another 96 hours, cooled to room temperature and the resulting solid separated by filtration yielding another 252 g of methyl 3-bromomethyl-4-nitrobenzoate. The solids were combined yielding a total of 411.1 g of methyl 3-bromomethyl-4-nitrobenzoate with minor amounts of the starting methyl 3-methyl-4-nitrobenzoate and methyl 3-dibromomethyl-4-nitrobenzoate. This solid was used as such in the next step.

c) Preparation of methyl 3-acetoxymethyl-4-nitrobenzoate.

In a 5-liter three-necked round-bottomed flask equipped with a reflux condenser, overhead stirrer and nitrogen inlet, was placed 411 g of the previously prepared methyl 3-bromomethyl-4-nitrobenzoate, 441 g of anhydrous potassium acetate and 2 l of glacial acetic acid. The resulting mixture was refluxed for 4 hours, cooled to room temperature and stirred overnight. The solvent was removed in a rotary evaporator and the resulting light yellow solid treated with a mixture of 2 l of ethyl acetate and 1 l of water. The organic phase was separated, washed with water (3×400 mL), brine (1×400 mL) dried over anhydrous magnesium sulfate and the solvent removed using a rotary evaporator. The crude reaction mixture was triturated with hexane and filtered yielding 318 g of the expected methyl 3-acetoxymethyl-4-nitrobenzoate. This compound was used as such in the next step.

d) Preparation of methyl 3-hydroxymethyl-4-nitrobenzoate.

In a 5-liter three-necked round-bottomed flask equipped with a reflux condenser, overhead stirrer and nitrogen inlet, was placed 318 g of the previously prepared methyl 3-acetoxymethyl-4-nitrobenzoate and 3.2 l of anhydrous methanol. To the resulting solution was bubbled in 40 g of hydrogen chloride and the resulting mixture was refluxed for 3 hours. After cooling to room temperature the solvent was removed using a rotary evaporator yielding 273 g of methyl 3-hydroxymethyl-4-nitrobenzoate as a yellow solid containing traces of methanol, which was used as such in the next step.

e) Preparation of methyl 3-formyl-4-nitrobenzoate.

In a 5-liter four-necked round-bottomed flask 1.5 l of methylene chloride was cooled to −78° C. Oxalyl chloride (164 g, 1.29 moles) was added slowly, followed by dropwise addition of 202 g (2.59 moles) of dry dimethylsulfoxide in 125 mL of methylene chloride, keeping the temperature below −70° C. After the addition was complete the reaction mixture was stirred at −78° C. for 30 minutes and 273 g (1.29 moles) of previously prepared methyl 3-hydroxymethyl-4-nitrobenzoate dissolved in 250 mL of methylene chloride was added dropwise. The reaction mixture was stirred an additional 30 minutes. Triethylamine (392 g 3.88 moles) in 125 mL of methylene chloride was added dropwise keeping the temperature below −65° C. The reaction mixture was warmed up slowly to room temperature and stirred overnight. The solvent was removed using a rotary evaporator and the resulting solid treated with a mixture of 2 l of ethyl acetate and 1 l of water. The organic phase was separated, filtered through diatomaceous earth, and washed sequentially with dilute aqueous hydrochloric acid (2×250 mL), water (2×250 mL), saturated aqueous sodium bicarbonate (2×250 mL), water (2×200 mL), brine (1×200 mL) and dried over anhydrous magnesium sulfate. The solvent was removed using a rotary evaporator. The crude reaction mixture was triturated with hexane and filtered yielding 234.1 g of the expected methyl 3-formyl-4-nitrobenzoate as a yellow solid. This compound was used as such in the next step.

f) Preparation of methyl 3-methoxyiminomethyl-4-nitrobenzoate.

To a well stirred mixture of 195 g of methyl 3-formyl-4-nitrobenzoate, 1 l methylene chloride and 370 mL of water was added sequentially 77.6 g of methoxylamine hydrochloride, 76.2 g of sodium acetate and 6.8 g of tetra-n-butylammonium hydrogen sulfate. The resulting mixture was stirred overnight at room temperature, then diluted with 2 l of ethyl ether. The organic phase was separated and washed sequentially with water (1×500 mL), 2% aqueous hydrochloric acid (2×500 mL), water (2×250 mL), and brine (1×250 mL); then dried over anhydrous magnesium sulfate. The solvent was removed using a rotary evaporator yielding 218.6 g of the expected methyl 3-methoxyiminomethyl-4-nitrobenzoate as a reddish oil that solidified upon standing, and which was used as such in the next step.

g) Preparation of methyl 4-amino-3-methoxyiminomethylbenzoate

In a 5-liter three-necked round-bottomed flask was placed 0.9 l of 5% aqueous acetic acid and 157 g (2.8 moles) of iron. To the resulting well-stirred mixture was added 166.6 g (0.7 moles) of the previously prepared methyl 3-methoxyiminomethyl-4-nitrobenzoate dissolved in 0.9 l of ethyl acetate followed by dropwise addition of 0.9 l of acetic acid while keeping the temperature below 35° C. The resulting mixture was stirred at 35° C. for 30 minutes and filtered through diatomaceous earth. The filtrate was poured into 5 l of water. The aqueous phase was separated and washed with ethyl ether (2×500 mL). The combined organic layers were washed sequentially with water (4×500 mL), saturated aqueous sodium bicarbonate (2×500 mL), water (2×500 mL), and brine (1×400 mL). The organic layer was dried over anhydrous magnesium sulfate and the solvent removed using a rotary evaporator yielding 130 g of the expected methyl 4-amino-3-methoxyiminomethylbenzoate.

h) Preparation of methyl 4-amino-3-chloro-5-methoxyiminomethylbenzoate.

In a 2-liter three-necked round-bottomed flask was placed 106 g (0.51 moles) of the previously prepared 4-amino-3-methoxyiminomethylbenzoate and 500 mL of acetonitrile. The resulting mixture was heated at 70° C. and 75.2 g (0.56 moles) of N-chlorosuccinimide was added portionwise while keeping the temperature below 80° C. After the addition was complete the reaction mixture was refluxed for 1 hour. The reaction mixture was cooled to room temperature and the solvent eliminated in a rotary evaporator. The crude product was dissolved in 5 l of ethyl acetate. The organic solution was washed with water (3×500 mL) and then brine, dried over magnesium sulfate. The reaction mixture was concentrated in a rotary evaporator to a slurry, triturated with hexane and filtered yielding the expected methyl 4-amino-3-chloro-5-methoxyiminomethylbenzoate as a yellow solid. This reaction was repeated using the same amounts yielding a total of 210.5 g of methyl 4-amino-3-chloro-5-methoxyiminomethylbenzoate, which was used as such in the next step.

i) Preparation of 4-amino-3-chloro-5-methoxyiminomethylbenzoic acid.

In a 5-liter three-necked round-bottomed flask was placed 210 g (0.86 moles) of the previously prepared 4-amino-3-chloro-5-methoxyiminomethylbenzoate, 1.71 of methanol and 462 g (1.73 moles) of 15% aqueous sodium hydroxide. The resulting mixture was refluxed for 3 hours, after which the reaction mixture was stirred overnight at room temperature. The reaction mixture was concentrated using a rotary evaporator. The crude reaction mixture was dissolved in 2 l of water. The resulting aqueous solution was washed once with 500 mL of ethyl acetate, cooled in an ice bath and acidified to pH=2 with concentrated hydrochloric acid. The expected 4-amino-3-chloro-5-methoxyiminomethylbenzoic acid precipitated as a light yellow solid which was separated by suction filtration. The filter cake was washed with a 1:2 mixture of ethyl ether and hexane yielding after drying 185.2 g (94% yield).

j) Preparation of 4-amino-3-chloro-5-methoxyiminomethylbenzoyl chloride.

In a 5-liter three-necked round-bottomed flask was placed 180 g of the previously prepared 4-amino-3-chloro-5-methoxyiminomethylbenzoic acid, 2 l of toluene, 3 mL of dimethylformamide and 104 g (64 mL) of thionyl chloride. The resulting mixture was heated at 70° C. for 2 hours, filtered while hot and the solvent removed using a rotary evaporator yielding 178.1 g of the expected 4-amino-3-chloro-5-methoxyiminomethylbenzoyl chloride.

k) Preparation of 3-amino-1-chloro-3-methyl-2-nentanone hydrochloride (Compound VIII, wherein $R_1$ is methyl and $R_2$ is ethyl)

i) Preparation of N-[3-(3-methyl-1-pentynyl)]trifluoroacetamide

In a 3 liter, four-necked, round-bottomed flask fitted with a mechanical stirrer, nitrogen inlet and thermometer was placed 234 grams (g) (1.75 mole) of 3-amino-3-methyl-1-pentyne hydrochloride and 1,000 mL of methylene chloride. To the resulting well-stirred mixture was added slowly 354 g (3.51 mole) of triethylamine (TEA) dropwise, keeping the temperature below 30° C. After the addition was completed, the reaction mixture was stirred 120 minutes followed by dropwise addition of 334.5 g (1.59 mole) of trifluoroacetic anhydride dissolved in 500 mL of methylene chloride at such a rate to keep the reaction temperature at 0° C. After the addition was completed the reaction mixture was stirred at room temperature overnight and concentrated in vacuo . The resulting slurry was washed with ethyl ether. The ethyl ether layer was washed sequentially with water, saturated aqueous sodium bicarbonate and brine, dried over anhydrous magnesium sulfate, treated with activated charcoal, and filtered through Celite® filter agent (available from Aldrich Chemical Company, St. Louis, Mo.). The solvent was eliminated under reduced pressure. The resulting crude product was treated with cold pentane, filtered, and dried yielding 255.5 g (83%) of the expected N-[3-(3-methyl-1-pentynyl)]trifluoroacetamide as a white solid.

ii) Preparation of 5-chloro-5-(dichloromethyl)-4-ethyl-4-methyl-2-trifluoromethyloxazoline hydrochloride:

In a 5 L, four-necked, round-bottomed flask fitted with a mechanical stirrer, a thermometer, and a gas inlet was dissolved 255.5 g (1.32 mole) of N-[3-(3-methyl-1-pentynyl)]trifluoroacetamide in 4,000 mL of methylene chloride. The resulting mixture was cooled to −30° C. and 235 g of chlorine was bubbled in over a 2 hour period. When the addition was completed the reaction mixture was stirred at −30° C. during 30 minutes and warmed to room temperature. The crude reaction mixture was evaporated in the rotary evaporator yielding the expected 5-chloro-5-(dichloromethyl)-4-ethyl-4-methyl-2-trifluoromethyloxazoline hydrochloride which was used as such in the next step.

iii) Preparation of 3-amino-1,1-dichloro-3-methyl-2-pentanone hydrochloride:

The 5-chloro-5-(dichloromethyl)-4-ethyl-4-methyl-2-trifluoromethyloxazoline hydrochloride prepared in the preceding step was dissolved in 1800 mL of methanol, 72 mL of water, and 190 mL of concentrated hydrochloric acid, warmed to 50° C., and stirred at that temperature overnight. The crude reaction mixture was cooled and poured into an ice/water/ethyl ether mixture. The phases were separated and the ether layer was extracted once with water. The ether was saved (organic I). The combined aqueous layers were washed once with ethyl ether, and the organic layer was combined with organic I (organic II). The aqueous layer was neutralized with saturated aqueous sodium bicarbonate and extracted twice with ethyl ether. The combined ether layers were washed with water, brine, dried over anhydrous magnesium sulfate, treated with activated charcoal, and filtered through Celite® filter agent. To the resulting colorless solution was bubbled in anhydrous hydrogen chloride keeping the temperature below 20° C. The resulting white solid was filtered and dried yielding 124.8 g of the expected 3-amino-1,1-dichloro-3-methyl-2-pentanone hydrochloride as a white solid. The ethyl ether filtrate was combined with organic II and concentrated in vacuo; the resulting residue (150 g) was taken in a mixture of methanol/water/concentrated hydrochloric acid and heated at 50° C. over the weekend. The previously described workup yielded another 51 g of 3-amino-1,1-dichloro-3-methyl-2-pentanone hydrochloride. The total amount obtained was 175.8 g (61% yield).

iv) Preparation of 3-amino-1-chloro-3-methyl-2-pentanone hydrochloride:

In a 2 L Parr™ bottle was placed 41 g of 3-amino-1,1-dichloro-3-methyl-2-pentanone hydrochloride, 0.8 g of 10% palladium over charcoal, and 400 mL of ethanol. The resulting mixture was shaken in a Parr™ apparatus at 50 psi for 3 hours. The crude reaction mixture was filtered through Celite® filter agent and evaporated in vacuo yielding a viscous oil, which was taken in 300 to 400 mL of ethyl acetate and stirred at room temperature for several hours. The expected 3-amino-1-chloro-3-methyl-2-pentanone hydrochloride crystallized as a white solid; 300 mL of hexane was added to the resulting suspension and filtered yielding 34 g (98%) of the expected 3-amino-1-chloro-3-methyl-2-pentanone hydrochloride.

The reaction was repeated starting with 41 g; 41 g; and 51 g of 3-amino-1,1-dichloro-3-methyl-2-pentanone hydrochloride yielding a total of 132.1 g (90% overall yield) of 3-amino-1-chloro-3-methyl-1-pentanone hydrochloride.

1) Preparation of 4-amino-3-chloro-5-methoxyiminomethyl-N-(3-chloro-1-ethyl-1-methyl-2-oxopropyl)benzamide (compound 2).

In a 5-liter three-necked round bottomed flask was placed 93 g of 3-amino-1-chloro-3-methyl-2-pentanone hydrochloride (compound VIII in which R1 is methyl and R2 is ethyl) and 885 mL of water. To the resulting solution were added 138.6 g of sodium bicarbonate followed by 500 mL of ethyl acetate. To the resulting well-stirred mixture was added 123.5 g of 4-amino-3-chloro-5-methoxyiminomethylbenzoyl chloride dissolved in 1000 mL of ethyl acetate at room temperature over a period of 50 minutes. After the addition was complete the reaction mixture was stirred at room temperature for 1 hour. The two phases were separated and the organic layer was washed with water (2×500mL), brine (1×500 mL), dried over anhydrous magnesium sulfate and the solvent eliminated in a rotary evaporator yielding the crude product as a brown oil. This oil was passed through a short silica gel column using methylene chloride as elution solvent. Evaporation of the solvent yielded 133.3 g of the expected 4-amino-3-chloro-5-methoxyiminomethyl-N-(3-chloro-1-ethyl-1-methyl-2-oxopropyl)benzamide as an off-white solid (mp 140–141° C.).

Compound 3

Compound 3 was prepared according to synthetic methods described in U.S. Pat. No. 5,254,584.

Compound 9

Compound 9 was prepared according to synthetic methods described in U.S. Pat. No. 5,304,572.

Compound 18

Compound 18 was prepared by reaction of the corresponding aromatic derivative (VII), in which R4 and R5 together form a fused ring, with 3-amino-1-chloro-3-methyl-2-pentanone hydrochloride (compound VIII in which R1 is methyl and R2 is ethyl) as illustrated above in Scheme A:

EXAMPLES

The following examples are provided in order to illustrate the method of the present invention.

Evaluation of Compounds for Control of Mixed Algae Culture

MIC values represent the Minimum Inhibitory Concentrations. The MIC is the lowest level of compound required to completely inhibit (repress) the growth of a given organism.

MIC studies were conducted using microtiter plate assays. In this method, a wide range of concentrations was tested by preparing two-fold serial dilutions of the compound in 96-well plastic microtiter plates. All liquid media transfers were performed with calibrated single or multichannel digital pipettes. Stock solutions of compounds were prepared in appropriate solvents and dispensed to the growth medium. All subsequent dilutions in plates were made using the desired growth medium; total volume of liquid in each well was 100 microliters.

The algal cultures used in the MIC assay were obtained from the Culture Collection of Algae at the University of Texas at Austin (UTEX). Microorganisms used as inocula were cultured in shaken liquid culture (Bristol's medium, pH 7.0, 25° C. (*Journal of Phycology,* 23s, 1–47, 1987) or Modified Allen's Media Formulation, described below) for one week or as needed to attain a desired cell mass. The cultures were then inoculated into the microtiter plates using a 96-prong multiple inoculator (5 microliter inoculum); each well received a standard suspension of biomass (5% inoculum). Plates were incubated at 25° C. under constant illumination (500 ft. candles). The extent of growth was determined under low magnification with the aid of a microtiter plate reader. Growth in each cell was monitored periodically and growth/no-growth was recorded after a designated period.

| Component | Concentration (mg/l) |
| --- | --- |
| $NaNO_3$ | 250 |
| $CaCl_2(2H_2O)$ | 31 |
| $MgSO_4(2H_2O)$ | 75 |
| NaCl | 25 |
| $KH_2PO_4$ | 175 |
| $K_2HPO4$ | 75 |
| $FeCl_3(6H_2O)$ | 7.5 |
| $Na_2(EDTA)$ | 10.3 |
| $Na_2B_4O_7(10H_2O)$ | 2.25 |
| $MnCl_2(4H_2O)$ | 0.90 |
| $ZnCl_2(7H_2O)$ | 0.11 |
| $CuCl_2(2H_2O)$ | 0.025 |
| $Na_2MoO_4(2H_2O)$ | 0.015 |
| $VOSO_4(2H_2O)$ | 0.015 |
| $CoCl_2(6H_2O)$ | 0.005 |

Using the above method with a mixed population of fresh water algae, the activity of a number of compounds was evaluated at one or two weeks, or both, after adding the compound to the algae. The results of the MIC test on nine example compounds are provided in the following table:

| Compound | MIC (ppm) @ 1 week | MIC (ppm) @ 2 weeks |
| --- | --- | --- |
| 1 | 125 | 250 |
| 3 | 250 | 63.0 |
| 4 | 250 | 125 |
| 6 | >250 | 63.0 |
| 7 | >250 | 250 |
| 10 | >250 | 125 |
| 11 | 125 | 63.0 |
| 12 | 125 | 125 |
| 8 |  | 50.0 |
| 13 |  | 12.5 |
| 14 |  | 50.0 |
| 15 |  | 50.0 |
| 16 |  | 3.1 |
| 17 |  | 0.8 |

These data indicate that the compounds have antialgal activity against fresh water algae.

Evaluation of Compounds for Control of *Dunaliella parva*

This test evaluates the Minimum Inhibitory Concentration (MIC) of a compound for control of the marine alga *Dunaliella parva* in enriched seawater at a pH of 8.2. The test is conducted using 96 well microtiter plates. Serial two-the fold dilutions of the test compound are made across the plate. All liquid media transfers were performed with calibrated single or multichannel digital pipettes. Stock solutions of compounds were prepared in appropriate solvents and dispensed to the growth medium. All subsequent dilutions in plates were made using the desired growth medium; total volume of liquid in each well was 100 microliters. The plates are incubated for 1 week under constant illumination (500 footcandles) and inspected for growth after 1 week using a mirrored microtiter plate reader. The MIC is the lowest concentration where no growth is seen. Each sample was run in triplicate and the median MIC reported.

The results of the MIC test on six example compounds are provided in the following table:

| Compound | MIC (ppm) |
|---|---|
| 2 | 25 |
| 5 | 1.6 |
| 8 | 6.2 |
| 9 | 12.5 |

These data indicate that the compounds have antialgal activity against marine algae.

Evaluation of Compounds for Control of Marine Fouling Organisms

Tests were conducted to determine the toxicity of the compounds of the method of the present invention to Artemia. Artemia are indicative of hard fouling organisms.

Substitute ocean water was prepared following ASTM Method D 1141-90. The water was sterilized by filtration through a 0.22 micron cellulose acetate membrane filter. San Francisco Bay Brand® *Artemia salina* cysts were purchased from a local aquarium supply store. The cysts were hatched in a 250 mL Erlenmeyer flask. The Artemia cysts (0.2 g) were weighed into a sterilized flask. One hundred mL of sterile ASTM sea water was added to the flask. The flask was placed on an orbital shaker set at approximately 150 rotations per minute and 28° C. After 24 hours, the contents of the flask were poured into a separatory funnel. The egg shells were separated from the Artemia nauplii (larvae), as the shells floated to the top. The nauplii were returned to the flask for another 24 hours shaking. The inoculum was prepared by pouring the nauplii into a crystallizing dish 48 hours after the cysts were originally placed on the shaker. After the nauplii congregated, they were taken up in a sterile serological pipette and transferred into another crystallizing dish. The suspension was stirred with a magnetic stirrer enough to keep the nauplii in suspension. Eighty mL of sterile sea water was added to the suspension. Using an eight channel microliter pipette loaded with wide bore pipette tips, 100 μL of the suspension was transferred into a column of a 96 well, flat bottom, tissue culture plate to determine the inoculum density. The number of nauplii in 3 to 4 wells was counted under a microscope. The number was averaged, and the inoculum was adjusted through further dilution, to 25 to 30 nauplii per 100 mL.

Stock solutions of the compounds to be tested were prepared on a weight to volume basis. Stock solutions were prepared at 40 times the highest concentration to be tested. Solvents were chosen based on the solubility of the compound to be tested. Solvents used were DMSO, acetone, or isopropanol. The solvents were tested to make sure that they had no effect on the test results.

Ninety six well, flat bottom, tissue culture plates were used for these tests. One hundred ninety μL of sterile ASTM sea water was added to column 1 of each plate. One hundred μl of sterile ASTM sea water was added to columns 2 through 12 of each plate. Ten μL of a stock solution of one compound to be tested was added to the first three wells of column 1. The next 2 wells were skipped, as they serve as untreated controls. Ten μL of a stock solution of a second compound to be tested was added to the last three wells of column 1. Serial dilutions were performed by mixing and transferring 100 μL from column 1 to column 2, then from column 2 to 3, and the process was continued until all 12 columns were diluted. One hundred μL from column 12 was discarded. One hundred μL of the stirring Artemia inoculum was added to each well of the plate. The test plate was covered with a plastic tissue culture plate lid and incubated for 24 hours at 25° C.

Plates were read under a low magnification microscope 24 and 48 hours after the nauplii were added to the plate. The highest dilution in which all of the nauplii are dead is the $LC_{100}$. Nauplii are considered alive if any movement is seen during the viewing period.

The results of the test, conducted in triplicate, on six example compounds are provided in the following table:

| Compound | 24 hr LC100 (ppm) | 48 hr LC100 (ppm) |
|---|---|---|
| 2 | >50, >50, >50 | 12.5, 12.5, 25 |
| 5 | >100, >100, >100 | 3.1, 0.8, 0.8 |
| 8 | > solubility limit | 100, 100, 50 |
| 9 | >100, >100, >100 | 12.5, 50, 1.6 |
| 18 | >100, >100, >100 | >100, >100, 100 |

These data indicate that many of the compounds of the method of this invention have marine antifoulant activity.

We claim:

1. A method for controlling algae, comprising applying to the locus of the algae an algicidally effective amount of one or more compounds of the formula:

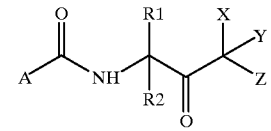

wherein:

A is selected from substituted and unsubstituted phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, benzyl, $(C_3-C_7)$cycloalkyl, $(C_1-C_6)$ alkyl, halo$(C_1-C_6)$alkyl, $(C_2-C_6)$alkenyl, halo$(C_2-C_6)$ alkenyl, $(C_2-C_6)$alkynyl, and halo$(C_2-C_6)$alkynyl wherein the substituents are independently selected from:
  a) one to four of halo, cyano, $(C_1-C_6)$alkyl, halo $(C_1-C_6)$alkyl, $(C_2-C_6)$alkenyl, halo$(C_2-C_6)$alkenyl, $(C_2-C_6)$alkynyl, halo$(C_2-C_6)$alkynyl, $(C_1-C_6)$ alkoxy, halo$(C_1-C_6)$alkoxy, $(C_1-C_6)$alkylthio, halo $(C_1-C_6)$alkylthio, nitro, $-NR^6R^7$, $-CR^8=NOR^9$, $NHCOOR^{10}$, $-CONR^{11}R^{12}$, $-COOR^{13}$;
  b) fused 5, 6, and 7-membered rings formed from two such substituents; and
  c) fused 5, 6 and 7-membered carbocyclic rings which may contain up to two heteroatoms selected from the group consisting of O, S, N, and P:

$R^1$ and $R^2$ are each independently selected from H, $(C_1-C_6)$alkyl, halo$(C_1-C_6)$alkyl, $(C_2-C_6)$alkenyl, halo $(C_2-C_6)$alkenyl, $(C_2-C_6)$alkynyl, or halo$(C_2-C_6)$ alkynyl provided that at least one of $R^1$ and $R^2$ is other than H;

R⁶ and R⁷ are each independently selected from H, (C₁–C₆)alkyl, and (C₁–C₆)alkylcarbonyl;

R⁸ is selected from H, (C₁–C₆)alkyl, (C₂–C₆)alkenyl, and (C2-C₆)alkynyl;

R⁹ is selected from H, (C₁–C₆)alkyl, (C₂–C₆)alkenyl, (C₂–C₆)alkynyl, and (C₁–C₄)alkylcarbonyl;

R¹⁰, R¹¹, R¹² and R¹³ are each independently selected from H, (C₁–C₆)alkyl, (C₂–C₆)alkenyl, and (C₂–C₆) alkynyl; and X, Y and Z are each independently selected from H, halo, cyano, thiocyano, isothiocyano and (C₁–C₆) alkylsulfonyloxy, provided that at least one of X, Y and Z is halo, cyano, thiocyano, isothiocyano or (C₁–C₆) alkylsulfonyloxy;

enantiomers and stereoisomers thereof; and acid addition salts thereof.

2. The method of claim 1 wherein the compound has the formula:

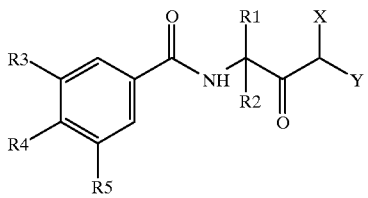

wherein:

R¹ and R² are each independently selected from H, (C₁–C₆)alkyl, halo(C₁–C₆)alkyl, (C₂–C₆)alkenyl, and (C₂–C₆)alkynyl, provided that at least one of R¹ and R² is other than H;

R³, R⁴, and R⁵ are each independently selected from:
  a) H, halo, cyano, (C₁–C₆)alkyl, halo(C₁–C₆)alkyl, (C₂–C₆)alkenyl, (C₂–C₆)alkynyl, (C₁–C₆)alkoxy, (C₁–C₆)alkylthio, halo(C₁–C₆)alkoxy, nitro, —NR⁶R⁷, —CR⁸=NOR⁹, NHCOOR¹⁰, —CONR¹¹R¹², and —COOR¹³; and
  b) two together form a fused 5, 6 or 7-membered carbocyclic ring which may contain up to two heteroatoms selected from the group consisting of: O, S, N, and P;

R⁶, R⁷, R⁸, R⁹, R¹⁰, R¹¹, R¹², and R¹³ are each independently selected from H and (C₁–C₆) alkyl; and X and Y are each independently selected from H, halo, cyano, thiocyano, isithiocyano and (C₁–C₆) alkysulfonyloxy, provided that at least one of X and Y is other than H.

3. The method of claim 2 wherein X is chloro; Y is H; R¹ is methyl; R² is methyl or ethyl; R³ and R⁵ are each independently selected from the group consisting of H, halo, methyl, nitro, cyano, —NR⁶R⁷, —CR⁸=NOR⁹ and —NHCOOR¹⁰; R⁴ is selected from H, —NR⁶R⁷, cyano, —CR⁸=NOR⁹, —NHCOOR¹⁰, COOR¹³, and (C₁–C₄) alkyl; and R⁶, R⁷, R⁸, R⁹, R¹⁰ and R¹³ are each independently H or (C₁–C₆) alkyl.

4. The method of claim 2 wherein R⁴ and R⁵ together form a fused 5, 6, or 7-membered ring containing up to two heteroatoms selected from the group consisting of O, S, N, and P.

5. The method of claim 1 wherein the compound has the formula:

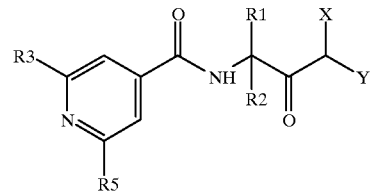

wherein

R¹ and R² are H, (C₁–C₆)alkyl, halo(C₁–C₆)alkyl, (C₂–C₆)alkenyl, and (C₂–C₆)alkynyl, provided that at least one of R¹ and R² is not H;

R³ and R⁵ are each independently selected from H, halo, cyano, (C₁–C₆)alkyl, halo(C₁–C₆)alkyl, (C₂–C₆) alkenyl, (C₂–C₆)alkynyl, (C₁–C₆)alkoxyl, (C₁–C₆) alkylthio, halo(C₁–C₆)alkoxyl, nitro, carboxyl, —NR⁶R⁷, —CR⁸=NOR⁹, NHCOOR¹⁰, —CONR¹¹R¹², and —COOR¹³;

R⁶, R⁷, R⁸, R⁹, R¹⁰, R¹¹, R¹², and R¹³ are H or (C₁–C₆) alkyl; and

X and Y are each independently selected from H, halo, cyano, thiocyano, isothiocyano and (C₁–C₆) alkysulfonyloxy, provided that at least one of X and Y is not H.

6. The method of claim 1 wherein the compound has the formula:

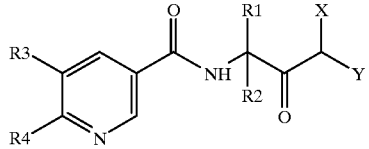

wherein R¹, ², R³, R⁴, X and Y are as defined in claim 1.

7. The method of claim 6 wherein R³ and R⁴ together form a fused 5, 6 or 7 membered carbocyclic ring containing up to two heteroatoms selected from the group consisting of O, S, N, and P.

8. The method of claim 1 wherein the compound has the structural formula:

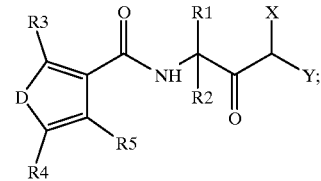

wherein:

D is O and S;

R¹ and R² are each independently selected from H, (C₁–C₆)alkyl, halo(C₁–C₆)alkyl, (C₂–C₆)alkenyl, and (C₂–C₆)alkynyl, provided that at least one of R¹ and R² is other than H;

R³, R⁴, and R⁵ are each independently selected from:
  a) H, halo, cyano, (C₁–C₆)alkyl, halo(C₁–C₆)alkyl, (C₂–C₆)alkenyl, (C₂–C₆)alkynyl, (C₁C₆)alkoxy, (C₁–C₆)alkylthio, halo(C₁–C₆)alkoxy, nitro, —$NR^6R^7$, —$CR^8=NOR^9$, $NHCOOR^{10}$, —$CONR^{11}R^{12}$, and —$COOR^{13}$; and b) $R^4$ and $R^5$ together form a fused 5, 6 or 7-membered carbocyclic ring which may contain up to two heteroatoms selected from the group consisting of: O, S, N, and P:

$R^6$, $R^7$, $R^8$, $R^9$, $R^{10}$, $R^{11}$, $R^{12}$, and $R^{13}$ are each independently selected from H and $(C_1-C_6)$ alkyl; and X and Y are each independently selected from H, halo, cyano, thiocyano, isithiocyano and $(C_1-C_6)$ alkysulfonyloxy, provided that at least one of X and Y is other than H.

9. A method to control organisms that cause hard fouling on submerged surfaces, comprising applying to the locus of the organism a compound of the method of claim 1.

10. The method of claim 1 wherein the algae are selected from individual species and mixed cultures of green algae, cyanobacteria, and marine algae.

* * * * *